US007799293B2

(12) United States Patent
Peterman et al.

(10) Patent No.: US 7,799,293 B2
(45) Date of Patent: Sep. 21, 2010

(54) ACTINIDE EXTRACTION METHODS

(75) Inventors: Dean R. Peterman, Idaho Falls, ID (US); John R. Klaehn, Idaho Falls, ID (US); Mason K. Harrup, Idaho Falls, ID (US); Richard D. Tillotson, Moore, ID (US); Jack D. Law, Pocatello, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 300 days.

(21) Appl. No.: 11/530,508

(22) Filed: Sep. 11, 2006

(65) Prior Publication Data

US 2010/0150798 A1 Jun. 17, 2010

(51) Int. Cl.
*B01D 11/04* (2006.01)
*C01G 56/00* (2006.01)
*C22B 60/00* (2006.01)
(52) U.S. Cl. .................. 423/8; 423/3; 423/10; 423/20; 423/21.1; 423/21.5; 568/8; 568/13; 568/14; 568/16; 210/634; 210/638; 210/749; 210/753
(58) Field of Classification Search .................. 423/3, 423/8–10, 20, 21.1, 21.5; 568/8, 13–14, 568/16–17; 210/634, 638, 639, 749, 753–755
See application file for complete search history.

(56) References Cited

U.S. PATENT DOCUMENTS 3,018,301 A    1/1962   Schrader (Continued)

FOREIGN PATENT DOCUMENTS

WO    2007037995    4/2007

(Continued)

OTHER PUBLICATIONS

Modolo, Giuseppe and Nabet, Sherif. "Thermodynamic Study on the Synergistic Mixture of Bis(chlorophenyl)dithiophosphinic Acid and Tris(2-ethylhexyl)phosphate for Separation of Actinides(III) from Lanthanides(III)." Solvent Extraction and Ion Exchange; May 2005, vol. 23 Issue 3, pp. 359-373.*

(Continued)

*Primary Examiner*—Scott Kastler
*Assistant Examiner*—Brian Walck
(74) *Attorney, Agent, or Firm*—TraskBritt (57) ABSTRACT

Methods of separating actinides from lanthanides are disclosed. A regio-specific/stereo-specific dithiophosphinic acid having organic moieties is provided in an organic solvent that is then contacted with an acidic medium containing an actinide and a lanthanide. The method can extend to separating actinides from one another. Actinides are extracted as a complex with the dithiophosphinic acid. Separation compositions include an aqueous phase, an organic phase, dithiophosphinic acid, and at least one actinide. The compositions may include additional actinides and/or lanthanides. A method of producing a dithiophosphinic acid comprising at least two organic moieties selected from aromatics and alkyls, each moiety having at least one functional group is also disclosed. A source of sulfur is reacted with a halophosphine. An ammonium salt of the dithiophosphinic acid product is precipitated out of the reaction mixture. The precipitated salt is dissolved in ether. The ether is removed to yield the dithiophosphinic acid.

13 Claims, 9 Drawing Sheets

U.S. PATENT DOCUMENTS

| | | | |
|---|---|---|---|
| 3,463,619 | A | 8/1969 | Ritter et al. |
| 4,308,214 | A | 12/1981 | Robertson et al. |
| 4,318,893 | A | 3/1982 | Bathellier et al. |
| 4,369,147 | A | 1/1983 | Michalski et al. |
| 4,412,053 | A | 10/1983 | Neilson et al. |
| 4,470,933 | A | 9/1984 | Michalski et al. |
| 4,523,009 | A | 6/1985 | Neilson et al. |
| 4,536,596 | A | 8/1985 | Savides et al. |
| 4,548,790 | A | 10/1985 | Horwitz et al. |
| 4,721,605 | A | 1/1988 | Brown et al. |
| 4,867,951 | A | 9/1989 | Smith et al. |
| 5,447,552 | A | 9/1995 | Mihaylov et al. |
| 5,475,146 | A | 12/1995 | Ayers et al. |
| 5,639,433 | A | 6/1997 | Yuan et al. |
| 5,826,161 | A | 10/1998 | Madic et al. |
| 5,908,805 | A | 6/1999 | Huser et al. |
| 5,966,584 | A | 10/1999 | Modolo et al. |
| 6,312,654 | B1 * | 11/2001 | Modolo et al. ............. 423/10 |
| 7,157,003 | B2 | 1/2007 | Baron et al. |
| 2004/0230079 | A1 | 11/2004 | Prakash et al. |
| 2005/0203314 | A1 | 9/2005 | Busacca et al. |

FOREIGN PATENT DOCUMENTS

| | | |
|---|---|---|
| WO | 2008088576 | 7/2008 |

OTHER PUBLICATIONS

Romanovskiy et al. "The Universal Solvent Extraction (UNEX) Process. I. Development of the UNEX Process Solvent for the Separation of Cesium, Strontium, and the Actinides From Acidic Radioactive Waste." Solvent Extraction and Ion Exchange; Jan. 2001, vol. 19 Issue 1, pp. 1-21.*

Modolo et al. "The separation of trivalent actinides from lanthanides by dithiophosphinic acids from HNO3 acid medium." Journal of Alloys and Compounds 271-273 (1998) 248-251.*

International Search Report for International Application WO 2008/088576 (PCT/US2007/073229), Mailed Aug. 7, 2008.

Written Opinion of the International Searching Authority, International Application No. PCT/US 06/35807, International filing date Sep. 13, 2006.

Ionova, Rabbe et al., Solvent Extraction and Ion Exchange, 19(3), (2001), pp. 391-414.

Modolo, G. Influence of the Purity and Irradiation Stability of Cyanex 301, etc., Journal of Radioanalytical and Nuclear Chemistry, vol. 228, (1998), pp. 83-88.

Cowley, A., Preparation and Properties of Bulky Secondary Phosphones, Inorg. Chem., (1983), 22, pp. 547-550.

Higgins, Vogel & Craig, Aromatic Phosphinic Acids and Derivatives, etc., Journal of the American Chemical Society, (1954), pp. 1864-1866.

Benner, S., Diphenylphosphinodithioic Acid, etc., Tetrahedron Letters, vol. 22, No. 20, (1981), pp. 1851-1854.

Bartlett & Meguerian, Reactions of Elemental Sulfur, etc., Journal of the American Chemical Society, vol. 78, (1956), pp. 3710-3715.

Casalnuovo et al., Ligand Electronic Effects in Asymmetric Catalysis, etc., Journal of the American Chemical Society, 116, (1994), pp. 9869-9882.

Casey, et al., Electron Withdrawing Substituents on Equatorial and Apical Phosphines, etc., Journal of the American Chem. Soc., 119, (1997), pp. 11817-11825.

Peters, G., Reactions of Secondary Phosphine Sulfides, Journal of the American Chemical Society, vol. 27, (1961), pp. 2198-2201.

Stuebe, et al., The Preparation and Reactions of Diphenylphosphinous Chloride, Journal of American Chemical Society, vol. 77, (1954), pp. 3526-3529.

Screttas et al., The Utilization of Organolithium Compounds, etc., Journal of American Chemical Society, vol. 27, (1962), pp. 2573-2577.

Hopkins, Vogel, Aromatic Phosphinic Acids and Derivatives, Journal of American Chemical Society, vol. 78, (1956), pp. 4447-4450.

Xie, Neilson et al., Organometallics, vol. 4, (1985), pp. 339-344.

Nash, K., A Comparison of New Reagents and Processes for Hydrometallurgical Processing of Actinides, Paper presented at Global 2001, Sep. 9-13, 2001, Paris, France. American Nuclear Society.

Hays, H., The Controlled Alkylation of Mono-n-alkylphosphines, Journal of American Chemical Society, vol. 31, (1966), pp. 3817-3820.

Kosolapoff, G., Some Variations of the Grignard Synthesis of Phosphinic Acids, Journal of the American Chemical Society, vol. 72, (1950), pp. 5508-5509.

Meier et al., Nonsymmetric palladium Complexes etc., Organometallics, vol. 22, (2003), pp. 3905-3914.

Guoxin et al., Investigation of the Extraction Complexes of Light Lanthanides, etc., Inorg. Chemistry, vol. 42, (2003), pp. 735-741.

Authors Unknown, Mitigation of Long Lived Actinides and Fission Products, ITU Annual Report (1997), pp. 83-95.

Dilworth & Wheatley, The Preparation and Coordination Chemistry of Phosphorus-Sulfur Donor Ligands, Coordination Chemistry Review, vol. 1999, (2000), pp. 89-158.

Pinkerton & Cavell, Synthesis and Characterization of Bis(trifluoromethyl)thiophosphinic Acid and its Anhydride, Journal of the American Chemical Society, vol. 94:6, (1972), pp. 1870-1874.

Cowley & Kemp, Preparation and Properties of Bulky Secondary Phosphines, Inorg. Chemistry, vol. 22, (1983), pp. 547-550.

Patel & Harwood, The Chemistry of Diphosphine Disulfides, The Journal of American Chemical Society, vol. 32, (1967), pp. 2999-3003.

Modolo & Odoj, Synergistic Selective Extraction of Actinides (III) Over Lanthanides, etc., Solvent Extraction and Ion Exchange, vol. 17(1), (1999), pp. 33-53.

Ionova et al., Mechanism of Trivalent Actinide/Lanthanide Separation Using Synergistic Mixtures, etc., New Journal of Chemistry, vol. 25, (2001), pp. 491-501.

Klaehn et al., U.S. Appl. No. 11/232,541, filed Sep. 21, 2005, Extraction Agent and Method for Forming an Extraction Agent for the Separation of Actinides From Lanthanides.

International Search Report for PCT/US06/35807 dated Aug. 3, 2007.

* cited by examiner

ACTINIDE EXTRACTION METHODS

GOVERNMENT RIGHTS

This invention was made with government support under DE-AC07-05ID14517 awarded by the United States Department of Energy. The government has certain rights in the invention.

CROSS-REFERENCE TO RELATED APPLICATION

This application is related to U.S. patent application Ser. No. 11/232,541, filed Sep. 21, 2005, now U.S. Pat. No. 7,704,468, issued Apr. 27, 2010, titled "Extraction Agent and Method for Forming an Extraction Agent for the Separation of Actinides From Lanthanides."

TECHNICAL FIELD

The invention pertains to methods of separating actinides, methods of separating actinides from lanthanides, separation compositions and methods for production and isolation of symmetric or asymmetric regio-specific/stereo-specific dithiophosphinic acids.

BACKGROUND OF THE INVENTION

Heretofore, the primary commercially available extractant employed to separate trivalent actinides from trivalent lanthanides has been bis-2,4,4-trimethylpentyl dithiophosphinic acid, having the trade name CYANEX®-301 (Cytec Technology Corp., Wilmington, Del.). This conventional extractant is an effective agent for the separation of trivalent actinides (Am(III), Cm(III), etc.) from lanthanides in an acidic medium.

While this extraction agent has worked with some degree of success, there are shortcomings with this compound that have detracted from its usefulness. Chief among these shortcomings is that this compound requires the use of mildly acidic processing conditions. In practice, the use of this compound requires complex adjustments to the aqueous process-feed that complicates the operation of this very complex extraction process, and tends to increase the amount of secondary waste material. In addition to the foregoing, it has long been known that CYANEX®-301 is easily decomposed in acidic solutions, further limiting its usefulness in production scale processes.

An extraction agent and method of extraction for actinides from lanthanides that avoids the shortcomings in the prior art compounds and methodology used heretofore is the subject matter of the present application. The method of extraction can additionally be utilized to separate actinides from one another.

SUMMARY OF THE INVENTION

In one aspect, the invention pertains to methods of separating at least one actinide from at least one lanthanide. A symmetric or asymmetric dithiophosphinic acid having regio-specificity and/or stereo-specificity is provided into an acidic medium containing at least one actinide and at least one lanthanide. The dithiophosphinic acid can have aromatic and/or alkyl groups having single or multiple functional groups.

In one aspect, the invention pertains to a separation method for separating a first actinide from a second actinide. An acidic medium containing a first actinide and a second actinide is provided. An organic solution containing at least one dithiophosphinic acid is contacted with an acidic medium and the first actinide is extracted into the organic solution.

In one aspect, the invention pertains to an actinide/lanthanide separation composition. The composition contains an aqueous phase and an organic phase. At least one dithiophosphinic acid is present in the composition, along with at least one actinide and at least one lanthanide.

In one aspect, the invention pertains to an actinide-actinide separation composition having an aqueous phase and an organic phase. The composition includes at least one dithiophosphinic acid and at least two actinides.

In one aspect, the invention pertains to a method of specifically producing either a symmetric or an asymmetric dithiophosphinic acid having regio-specificity and/or stereo-specificity. A source of sulfur is reacted with a phosphine to produce a dithiophosphinic acid product. A reaction mixture is formed and an excess of ammonium carbonate is added to the reaction mixture. An ammonium salt of the dithiophosphinic acid is precipitated out of the reaction mixture. The precipitated ammonium salt is dissolved in ether. The ether phase is contacted with hydrochloric acid and the ether is removed to yield the dithiophosphinic acid.

BRIEF DESCRIPTION OF THE DRAWINGS

Preferred embodiments of the invention are described below with reference to the following accompanying drawings.

FIG. 1 is a graph showing distribution ratios for americium and europium as a function of aqueous phase acid concentration.

DETAILED DESCRIPTION OF THE INVENTION

This disclosure of the invention is submitted in furtherance of the constitutional purposes of the U.S. Patent Laws "to promote the progress of science and useful arts" (Article 1, Section 8).

In general, the invention encompasses an extraction agent, methods of producing the extraction agent, and extraction methodology. The extraction includes methodology that can be utilized for extracting an actinide from one or more differing actinides and/or extracting an actinide from one or more lanthanides.

The extraction agent (extractant) can typically comprise a symmetric or asymmetric dithiophosphinic acid. The dithiophosphinic acid can contain alkyl and/or aromatic groups having various functional groups. The dithiophosphinic acid can preferably be prepared to have at least two regio-specific and/or stereo-specific organic moieties. These may include a first organic moiety that is an aromatic having a first functional group selected from the group consisting of substituted or non-substituted alkyls, alkenyls, alkynyls, single-ring aryls, multi-ring aryls, or mixtures thereof. The substitutions can be, for example, oxygen, nitrogen, fluorine, chlorine, bromine, iodine, boron, gallium, silicon, germanium, phosphorus, arsenic, antimony, sulfur, selenium, tellurium, and oxides thereof. Multiple substitutions may be present on a given functional group.

The second organic moiety can be either an aromatic or an alkyl. The second moiety has a second functional group which can be the same as or can differ from the first functional group and can be selected from the group consisting of substituted or non-substituted alkyls, alkenyls, alkynyls, single-ring aryls, multi-ring aryls, or mixtures thereof. The substitutions can be, for example, oxygen, nitrogen, fluorine, chlorine, bromine, iodine, boron, gallium, silicon, germanium, phosphorus, arsenic, antimony, sulfur, selenium, tellurium, and oxides thereof. Multiple substitutions may be present on the second functional group.

In particular instances, a symmetric extractant can be a bis-phenyl dithiophosphinic acid. Preferably, the extraction agent is bis-(ortho-trifluoromethylphenyl) dithiophosphinic acid (hereinafter referred to as o-$CF_3$), shown below.

Bis-(o-trifluoromethylphenyl)dithiophosphinic acid; (o-$CF_3$)

The o-$CF_3$ (or alternative regio-specific/stereo-specific dithiophosphinic acid) utilized for the invention can be prepared by, for example, utilizing methodology as set forth in co-pending U.S. patent application Ser. No. 11/232,541, entitled Extraction Agent and Method for Forming an Extraction Agent for the Separation of Actinides from Lanthanides, the contents of which is hereby incorporated by reference. As set forth in the co-pending application, various reagents can be reacted to produce halophosphines that are symmetric or asymmetric, and which contain aromatic and/or alkyl groups with various regio-specific/stereo-specific functional groups, for example, bis-(ortho-trifluoromethylphenyl) chlorophosphine. The halophosphine can be reduced to the phosphine by various metal hydrides. The corresponding phosphine can then be reacted with a source of sulfur to produce a dithiophosphinic acid product that is symmetric or asymmetric, containing aromatic/alkyl groups having various functionalities. An example of a symmetric dithiophosphinic acid that can be produced using such methodology is bis-(ortho-trifluoromethylphenyl)dithiophosphinic acid. The product can be in acid form as set forth in the co-pending application. The product can be collected by alternative methodology such as distillation as described in the co-pending application, or by salt precipitation as set forth below.

Upon formation of the final phosphinic acid product utilizing methodology as set forth in the co-pending application, the product can be precipitated as its corresponding salt from the reaction mixture. The reaction mixture containing the acid product can be transferred to an appropriate flask, preferably while still hot. The original reaction flask can be washed with an organic solvent such as, for example, toluene, which is then added to the flask into which the reaction mixture has been transferred. Subsequently, while maintaining the reaction mixture at a temperature near boiling, an excess of an appropriate salt such as, for example, ammonium carbonate (($NH_4$)$_2CO_3$) is added to the reaction mixture. The corresponding product, phosphinate salt, is then precipitated out of the hot mixture as a solid. The salt can be collected by filtration over an appropriate filter such as, for example, filter paper.

The resulting precipitate can be washed with an appropriate organic solvent such as, for example, toluene. The salt can be allowed to dry and can subsequently be converted to its corresponding acid by, for example, dissolving the salt in an appropriate organic solvent such as diethyl ether and an acid such as, for example, aqueous hydrochloric acid. The organic solvent layer can be separated from the aqueous phase to collect the product acid in the ether/organic layer. Further purification can be achieved utilizing appropriate purification techniques, such as recrystallization in hexane or other appropriate organic solvents.

EXAMPLE

Salt Precipitation of Product

A dark-green reaction mixture containing o-$CF_3$ was produced utilizing methodology as set forth in the co-pending application. The reaction mixture was transferred to a 250 mL Erlenmeyer flask equipped with a magnetic stir bar while the mixture was still hot. Seventy-five mL of toluene was utilized to wash the reaction flask and was subsequently transferred into the Erlenmeyer flask. A hot plate/stirrer was utilized to keep the toluene stirring at a temperature near boiling. A slight excess of ammonium carbonate (0.75 g, 0.008 mol) was slowly added to the reaction mixture. The ammonium salt (o-($CF_3$)$C_6H_4$)$_2PS_2$($NH_4$) slowly precipitated out of the hot toluene as a white powdery solid. The solution remained heated and was stirred for about 1 hour. The ammonium salt was filtered through fluted filter paper while the solution was still hot. Additional chilled toluene was utilized to wash the precipitate. The ammonium salt was collected on a watch glass and allowed to air dry overnight. Fifty mL of diethyl ether was provided within a 125 mL separatory funnel and subsequently 25 mL of 4.0 M hydrochloric acid was added to the separatory funnel. The ammonium salt product was introduced into the separatory funnel and was shaken vigorously to dissolve the salt into the diethyl ether. After the ammonium salt was dissolved, the diethyl ether layer was isolated and the water layer was washed twice with 25 mL of diethyl ether, which was then combined with the originally separated diethyl ether layer. The ether was then removed from the product o-$CF_3$ utilizing a roto-evaporator. The resulting product was a light-green solid and the overall yield of the isolated product was about 75%. The product was subsequently recrystallized in hexanes to result in light-green prismatic crystals.

The yield, physical and nuclear magnetic resonance (NMR) characteristics for the resulting bis-(o-trifluoromethylphenyl)dithiophosphinic acid (o-CF$_3$) were as follows: [~40% overall yield; mp=93° C.-94° C.; bp=0.07-0.125 mmHg/150° C.-160° C.; $^{31}$P NMR δ (CDCl$_3$)=(t, J$_{PH}$=19.6 Hz) 58.1; $^{19}$F NMR δ (CDCl$_3$)=(s) −55.7; $^{1}$H NMR δ (CDCl$_3$)= (dd, J$_{PH}$=18.0 Hz, J$_{FH}$=9.0 Hz, H) 8.43, (m, 3H) 7.65-7.85, (s, H) 3.31; $^{13}$C NMR δ (CDCl$_3$)=(doublet, J$_{PC}$=78.5 Hz, ipso) 134.3, (doublet, J$_{PC}$=12.8 Hz, ortho) 134.2, (doublet, J$_{PC}$=3.0 Hz, para) 132.1, (doublet, J$_{PC}$=14.3 Hz, meta) 131.7, (doublet of quartets, J$_{PC}$=6.0 Hz, J$_{CF}$=38.5 Hz, ortho) 129.7, (multiplet, meta) 128.0, (quartet, J$_{CF}$=274.7 Hz, CF$_3$) 123.4].

From the results of the alternative isolation method set forth above, it can be noted that for particular products, such as o-CF$_3$, the salt precipitation method can be preferred since such results in increased yields relative to distillation techniques described in the co-pending application. Although the methodology above is described in terms of particular dithiophosphinic acids it is to be understood that the methodology can be utilized to produce alternative dithiophosphinic acids.

Extraction methodology of the invention can be utilized to separate one or more actinides from one or more lanthanides and/or to separate one actinide from one or more additional differing actinides. Such methodology typically involves formation of a separation composition having an organic phase and an aqueous phase. The aqueous phase of the separation composition is preferably acidic (having a pH of less than about 7). Where the separation involves extraction of one or more actinides from lanthanides, the pH of the aqueous phase is typically greater than about 2. However, where two or more actinides are to be separated from lanthanides, pH values of less than or equal to 2 can be utilized in particular instances to selectively extract a specific actinide, while leaving additional actinides and lanthanides in the aqueous phase (discussed more fully below).

Extraction methodology in accordance with the invention can be performed by dissolving the dithiophosphinic acid to be used as extractant in an appropriate organic solvent. Where an actinide-lanthanide separation is to be conducted, an acidic aqueous phase is provided having a first actinide and a first lanthanide. The aqueous phase may comprise a second or multiple additional actinides. The aqueous phase may also contain a second lanthanide or multiple lanthanides in addition to the first lanthanide. Once formed, the organic solution containing the extractant can be added directly to the aqueous solution containing the actinide to be extracted. A complex is then formed that contains the extractant and extracted metal. This complex is present in the organic phase and can be separated from non-extracted metals by removal of the organic phase from the two-phase separation composition.

In particular instances, the extractant can preferably be bis-(ortho-trifluoromethylphenyl)dithiophosphinic acid. This compound can be used independently or in combination with one or more additional dithiophosphinic acid extractants. Studies utilizing the present methodology indicate that independent utilization of o-CF$_3$ is sufficient to extract one or more actinides from one or more lanthanides and additionally indicate that specific actinides such as Am(III) can be selectively extracted from additional actinides such as Cm(III). Accordingly, extractions in accordance with the invention can efficiently separate one or both of Am(III) and Cm(III) from a composition containing one or more lanthanides and where a solution contains both Am(III) and Cm(III), the extraction methodology can be utilized to selectively remove Am(III) from Cm(III).

The results of tests utilizing the methodology of the invention additionally indicated that bis-(ortho-trifluoromethylphenyl)dithiophosphinic acid has improved separation efficiency and extractant stability relative to conventional actinide/lanthanide extractants. As presented below, the extractant stability extends to methodology where the o-CF$_3$ is dissolved in a suitable organic diluent and wherein the aqueous solution contains significant concentrations of acid. The extractant additionally is capable of efficiently separating Am(III) from Eu(III) in such an extraction composition.

The organic solvent is not limited to any particular solvent and can preferably be a polar hydrophobic solvent. In particular instances where the extractant comprises o-CF$_3$, an appropriate preferred solvent can be trifluoromethylphenyl sulfone (henceforth referred to as FS-13). It is to be understood, however, that the invention contemplates utilization of alternative polar hydrophobic solvents.

Although not limited to particular concentrations, the organic solution can typically contain an appropriate amount of extractant to fully extract the desired actinide(s) from the acidic aqueous phase into the organic phase of the resulting two-phase separation composition. An appropriate concentration for a particular extractant and solvent system can be determined based upon the solubility limit of the extractant in the particular solvent utilized. Where the extractant comprises o-CF$_3$, an appropriate extractant concentration can be 0.1 M of o-CF$_3$ in FS-13. The acidic aqueous solution is contacted with this organic solution containing the extractant to form the biphasic solvent system extraction composition.

The pH of the aqueous phase is not limited to a particular value and can depend upon the particular actinides and/or lanthanides present in the solution. The distribution ratio D$_M$ and separation factor S can be utilized to determine separation efficiency of a particular separation and can assist in determining appropriate pH values of the aqueous phase. The distribution ratio D$_M$ is utilized to quantify the separation of a component of a solution in a biphasic solvent system. In the case of actinide/lanthanide separations (or actinide/actinide separations) the distribution ratio is defined as the sum of the concentrations of metal containing species in the organic phase divided by the sum of the concentrations of metal containing species in the aqueous phase: D$_M$=Σ[M$^{n+}$]org/Σ[M$^{n+}$]aq. The separation factor is defined as the ratio of the distribution ratios for the metal species of interest: S=D$_M$/D$_{M'}$.

An example separation quantification study was performed in a biphasic solvent system composition for Am(III) and Eu(III) as a function of aqueous phase nitric acid concentration. In the extraction composition, the extractant forms a complex with metal ions to form an extracted metal complex present in the organic phase. The data presented in Table 1 shows the distribution ratios (average of three independent determinations for Am (D$_{Am}$) and Eu (D$_{Eu}$) as a function of nitric acid concentration. The aqueous phase contained 0.001 M Eu(NO$_3$)$_3$ and 1.0 M [NO$_3^-$]$_{total}$ as sodium nitrate in varying concentrations of HNO$_3$. Unless otherwise noted, the organic phase composition used in these studies was 0.1 M o-CF$_3$ dissolved in FS-13.

The logarithms of the distribution data shown in Table 1 are plotted in FIG. 1. The type of plot presented in FIG. 1 is useful for examination of the stoichiometry of extracted metal complex. The data presented in Table 1 and FIG. 1 indicates that Am(III) is extracted (D$_{Am}$>1) by o-CF$_3$ at pH values of ≧2.00 and is not extracted (D$_{Am}$<1) at pH values<2.0.

TABLE 1

Am and Eu Distribution Ratios

| pH | [HNO$_3$], M | D$_{Am}$ | D$_{Eu}$ |
|---|---|---|---|
| 2.30 | 5.0 × 10$^{-3}$ | 1.17E+02 | 1.10E-03 |
| 2.14 | 7.2 × 10$^{-3}$ | 5.06E+01 | 3.52E-04 |
| 2.00 | 1.0 × 10$^{-3}$ | 1.47E+01 | 1.61E-04 |
| 1.32 | 4.8 × 10$^{-2}$ | 9.92E-02 | 9.48E-05 |
| 1.02 | 9.6 × 10$^{-2}$ | 1.06E-02 | 8.73E-05 |

The same data set shows that Eu(III) is not extracted by o-CF$_3$ at any of the pH values studied. The linear equation presented in FIG. 1 shows that the slope of the linear regression of log-log data plot is approximately −3.2. This indicates that the extracted complex contains three o-CF$_3$ ligands for each Am(III) metal center. This stoichiometry is consistent with the expected acidic ion exchange extraction mechanism.

Additional studies were performed to determine distribution ratios as a function of aqueous phase nitric acid concentration for Cm(III), (D$_{Cm}$). The aqueous phase contained 0.001 M Eu(NO$_3$)$_3$ and 1.0 M [NO$_3^-$]$_{total}$ as sodium nitrate in varying concentrations of HNO$_3$. The organic phase was 0.1 M o-CF$_3$ dissolved in FS-13. The logarithms of the distribution data shown in Table 2 are plotted in FIG. 2. Such study was performed using only $^{244}$CM radio tracer.

TABLE 2

Cm Distribution Ratios

| pH | [HNO$_3$], M | D$^{244}$Cm |
|---|---|---|
| 2.45 | 3.6 × 10$^{-3}$ | 8.67E+00 |
| 2.14 | 7.2 × 10$^{-3}$ | 2.66E+00 |
| 1.92 | 1.2 × 10$^{-2}$ | 7.50E-01 |
| 1.01 | 9.8 × 10$^{-2}$ | 5.42E-03 |

Figure 2:
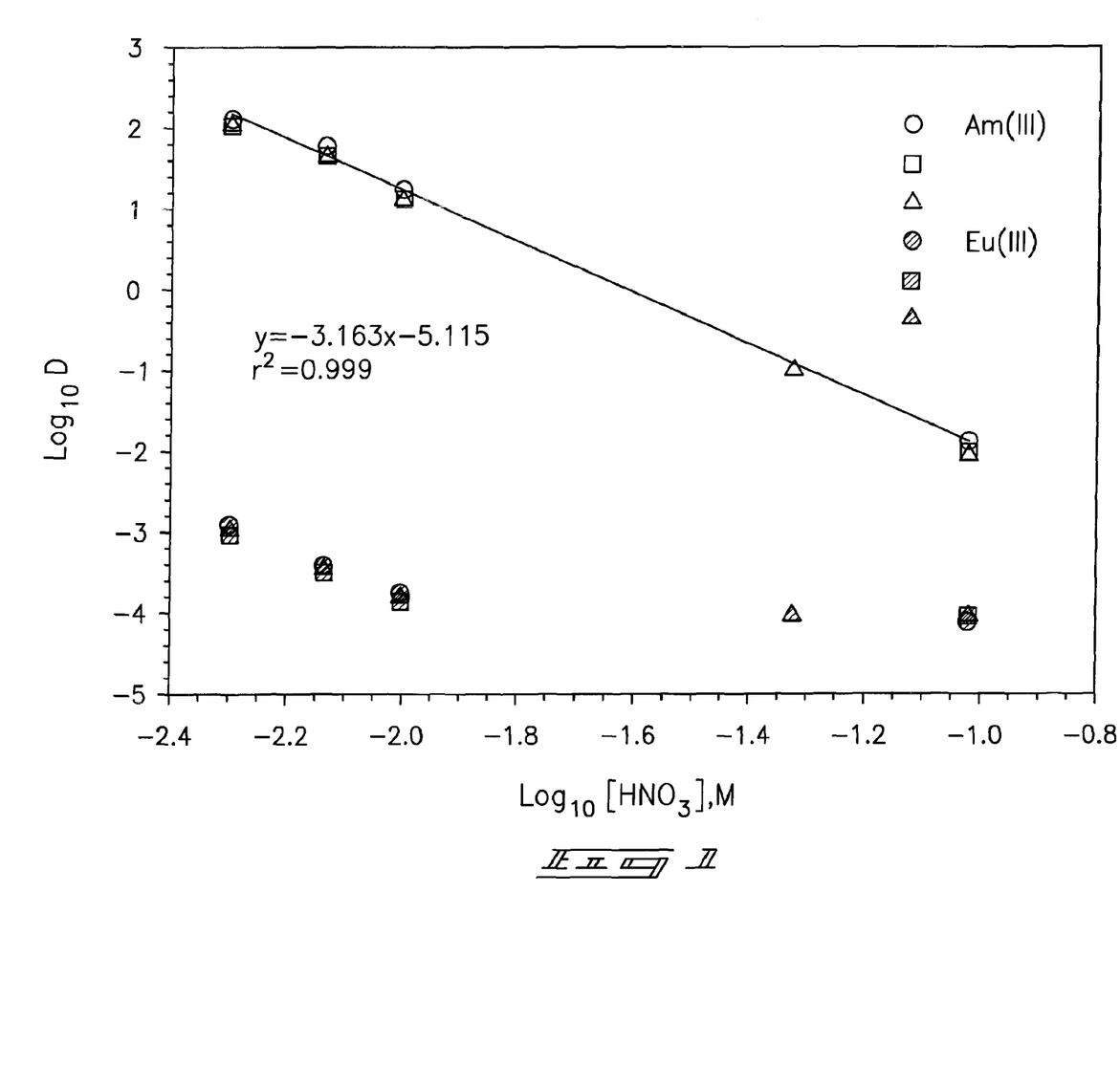
FIG. 2 is a graph showing distribution ratios for curium as a function of aqueous phase acid concentration.

The data presented in Table 2 and FIG. 2 indicates that Cm(III) is extracted (D$_{Cm}$>1) by o-CF$_3$ at pH values of >2.14 and is not extracted (D$_{Cm}$<1) at pH values<1.92. The linear equation presented in FIG. 2 indicates that the slope of linear regression of log-log data plot is approximately −2.3.

Figure 3:
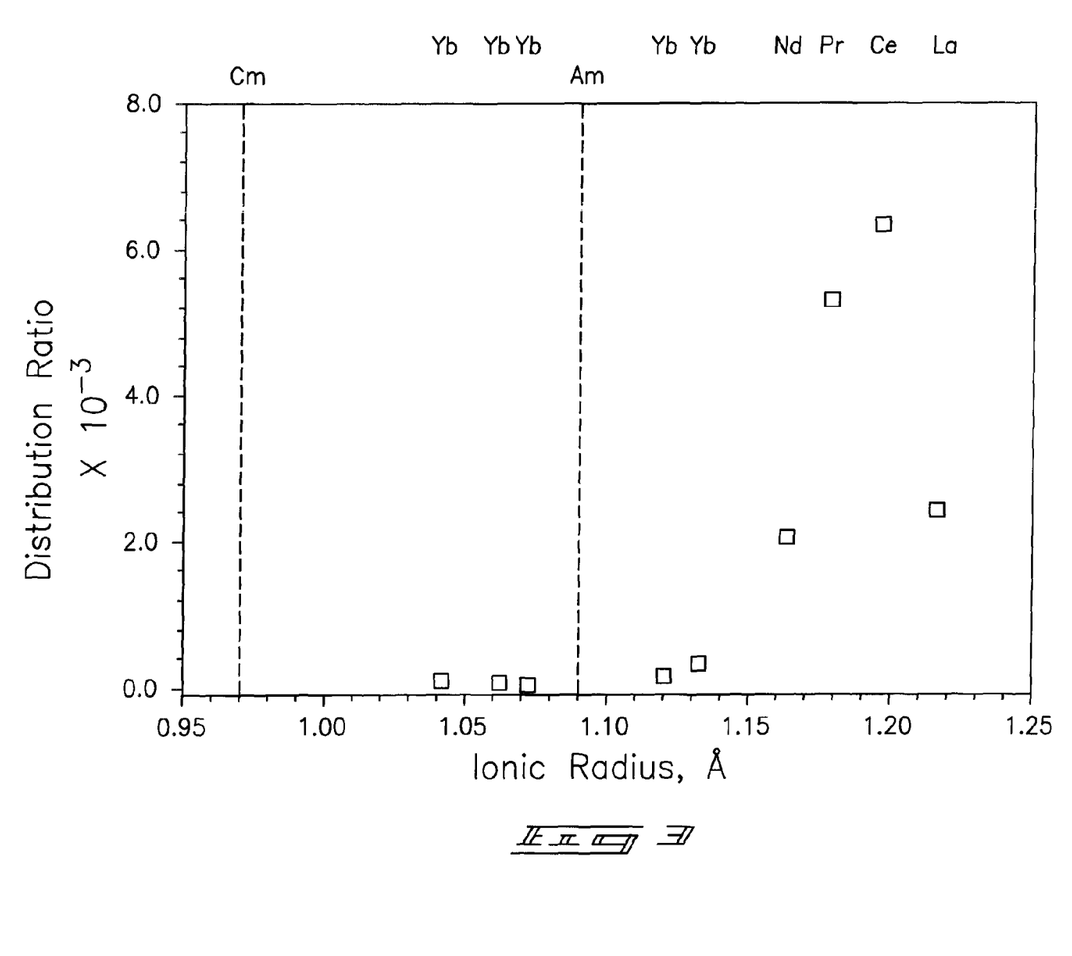
FIG. 3 is a graph showing distribution ratios for the lanthanide ions as a function of ionic radius.

The lanthanides present in the extraction composition are not limited to particular elements. Studies utilizing the present methodology indicate that one or more actinides can be separated from compositions comprising one or multiple lanthanides. Distribution ratios D$_{Ln}$ for lanthanide ions determined by methodology of the invention are presented in Table 3 and in FIG. 3.

TABLE 3

Lanthanide Distribution Ratios

| Ln(III) | D$_{Ln}$ |
|---|---|
| La | 2.41E-03 |
| Ce | 6.32E-03 |
| Pr | 5.31E-03 |
| Nd | 2.05E-03 |
| Pm | n.d. |
| Sm | 3.36E-04 |
| Eu | 1.57E-04 |
| Gd | n.d. |
| Tb | n.d. |
| Dy | n.d. |
| Ho | 4.36E-05 |
| Er | 7.59E-05 |
| Tm | n.d. |

TABLE 3-continued

Lanthanide Distribution Ratios

| Ln(III) | D$_{Ln}$ |
|---|---|
| Yb | 9.10E-05 |
| Lu | n.d. |

The lanthanide distribution ratios were calculated from the results of inductively coupled plasma mass spectrometry (ICP-MS) analysis of the aqueous phase (0.01 M HNO$_3$+1.0 M NaNO$_3$) and the organic phase (0.1 M o-CF$_3$ in FS-13) following a single phase contact. In each case, the calculated values of D$_{Ln}$ are significantly less than one. These results indicate that the o-CF$_3$ ligand dissolved in FS-13 does not extract any lanthanide ions. The distribution ratios for Eu(III), (D$_{Eu}$) determined from radiometric and ICP-MS analysis agree to within the experimental error. Accordingly, the lanthanide distribution ratios appear to be sufficiently low to allow efficient separation of actinides from any lanthanide or combination of lanthanides present in the composition.

Additional studies were performed to determine distribution ratios for Am(III) and Eu(III) as a function of nitrate ion concentration in the aqueous phase. The organic phase was 0.1 M o-CF$_3$ in FS-13. The aqueous phase was 0.001 M Eu(NO$_3$)$_3$, 0.010 M HNO$_3$ and varying concentrations of NO$_3^-$ as sodium nitrate. The results of such studies are presented in Table 4 and plotted in FIG. 4. The nitric acid concentration was maintained at 0.010 M HNO$_3$ for these experiments.

TABLE 4

Am and Eu Distribution Ratios as a Function of [NO$_3^-$]

| [NO$_3$], M | logD$_{Am}$ | logD$_{Eu}$ |
|---|---|---|
| 0.00 | 1.13 | -3.83 |
| 0.80 | 1.13 | -3.93 |
| 0.60 | 1.15 | -3.71 |
| 0.40 | 1.17 | -3.58 |
| 0.20 | 1.20 | -3.81 |

Figure 4:
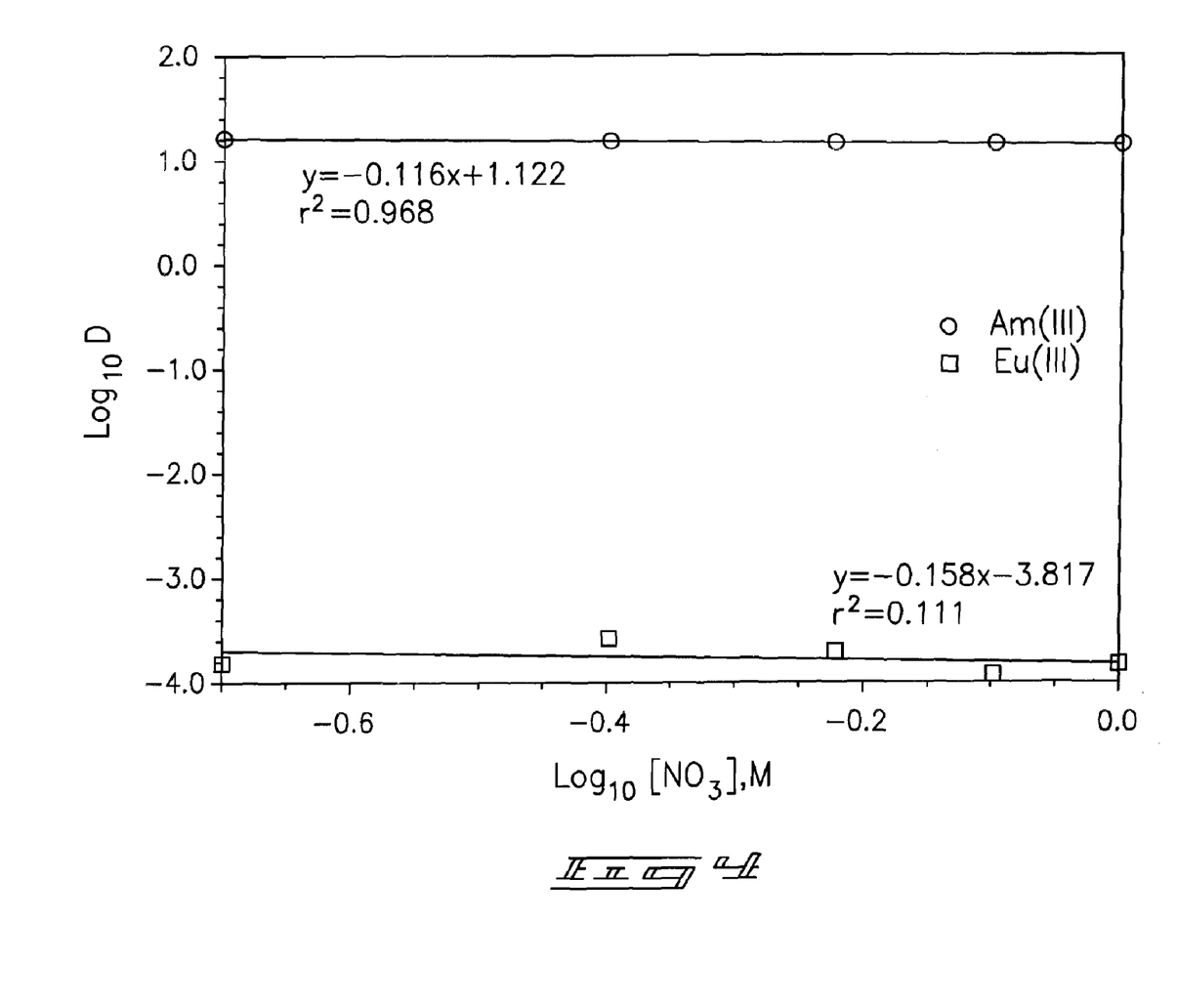
FIG. 4 shows distribution ratios for americium and europium as a function of aqueous phase nitrate ion concentration.

The data presented in Table 4 and FIG. 4 indicates that there is not significant dependence of the measured distribution ratios on the aqueous phase nitrate ion concentration. This indicates that the nitrate ion is not present in the Am(III)-(o-CF$_3$)$_n$ complex present in the organic phase.

Figure 5:
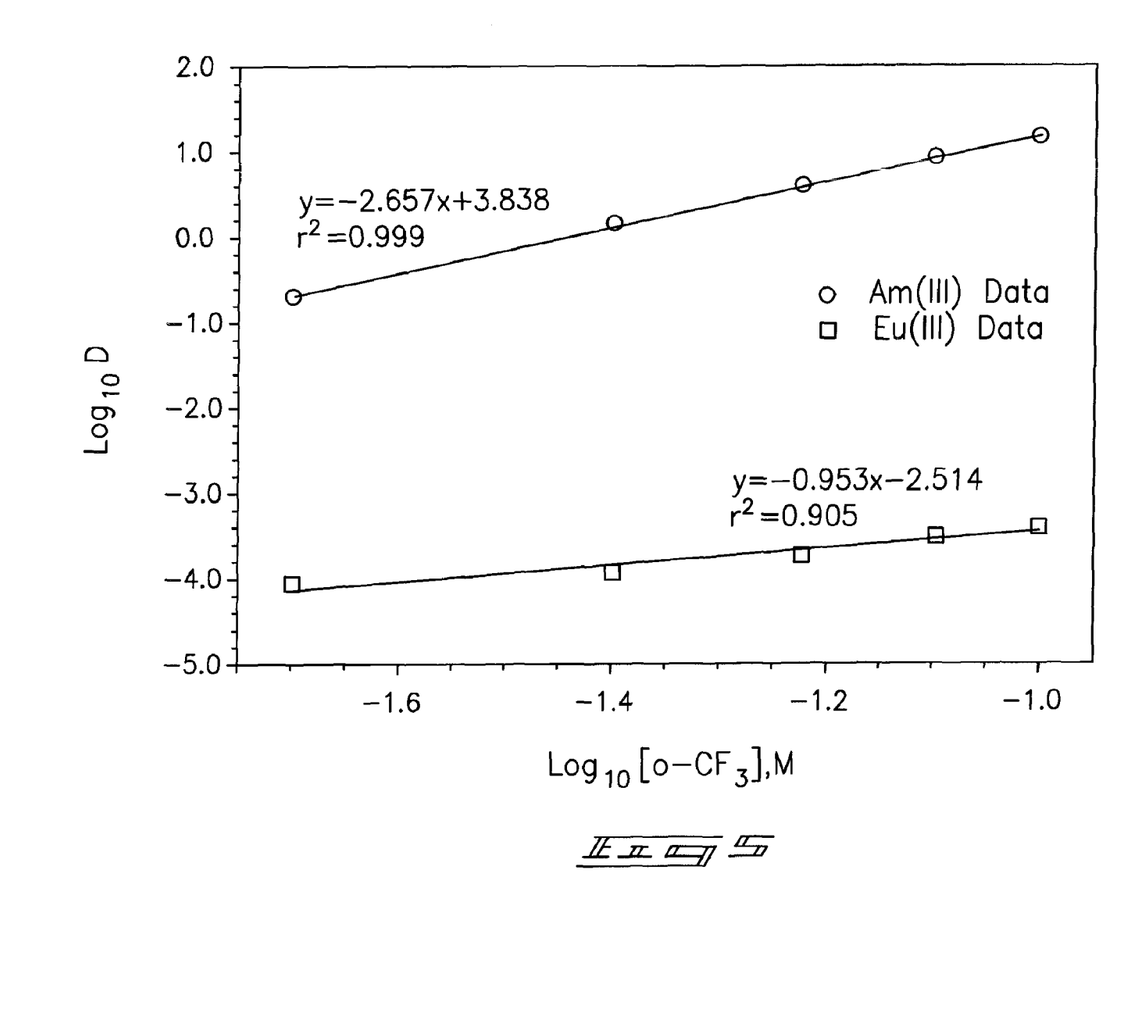
FIG. 5 is a graph showing distribution ratios for americium and europium as a function of organic phase bis-(ortho-trifluoromethylphenyl) dithiophosphinic acid concentration.

Further studies were performed to determine distribution ratios for Am(III) and EU(III), determined as a function of o-CF$_3$ concentration in the organic phase. The organic phase utilized varying concentrations of o-CF$_3$ in FS-13. The aqueous phase was 0.001 M Eu(NO$_3$)$_3$, 0.010 M HNO$_3$ and 1 M NO$_3^-$ as sodium nitrate. The results of such studies are presented in Table 5 and plotted in FIG. 5. The nitric acid concentration was maintained at 0.010 M HNO$_3$ for these experiments. The results of the linear regression of the log-log data indicate that approximately three o-CF$_3$ ligands are associated with each Am(III) metal ion in the organic phase.

TABLE 5

Am and Eu Distribution ratios as a Function of [o-CF$_3$]

| log[o-CF$_3$], M | logD$_{Am}$ | logD$_{Eu}$ |
|---|---|---|
| -1.00 | 1.16 | -3.41 |
| -1.10 | 0.93 | -3.53 |

TABLE 5-continued

Am and Eu Distribution ratios as a Function of [o-CF$_3$]

| log[o-CF$_3$], M | logD$_{Am}$ | logD$_{Eu}$ |
|---|---|---|
| −1.22 | 0.59 | −3.73 |
| −1.40 | 0.16 | −3.94 |
| −1.70 | −0.70 | −4.06 |

Figure 6:
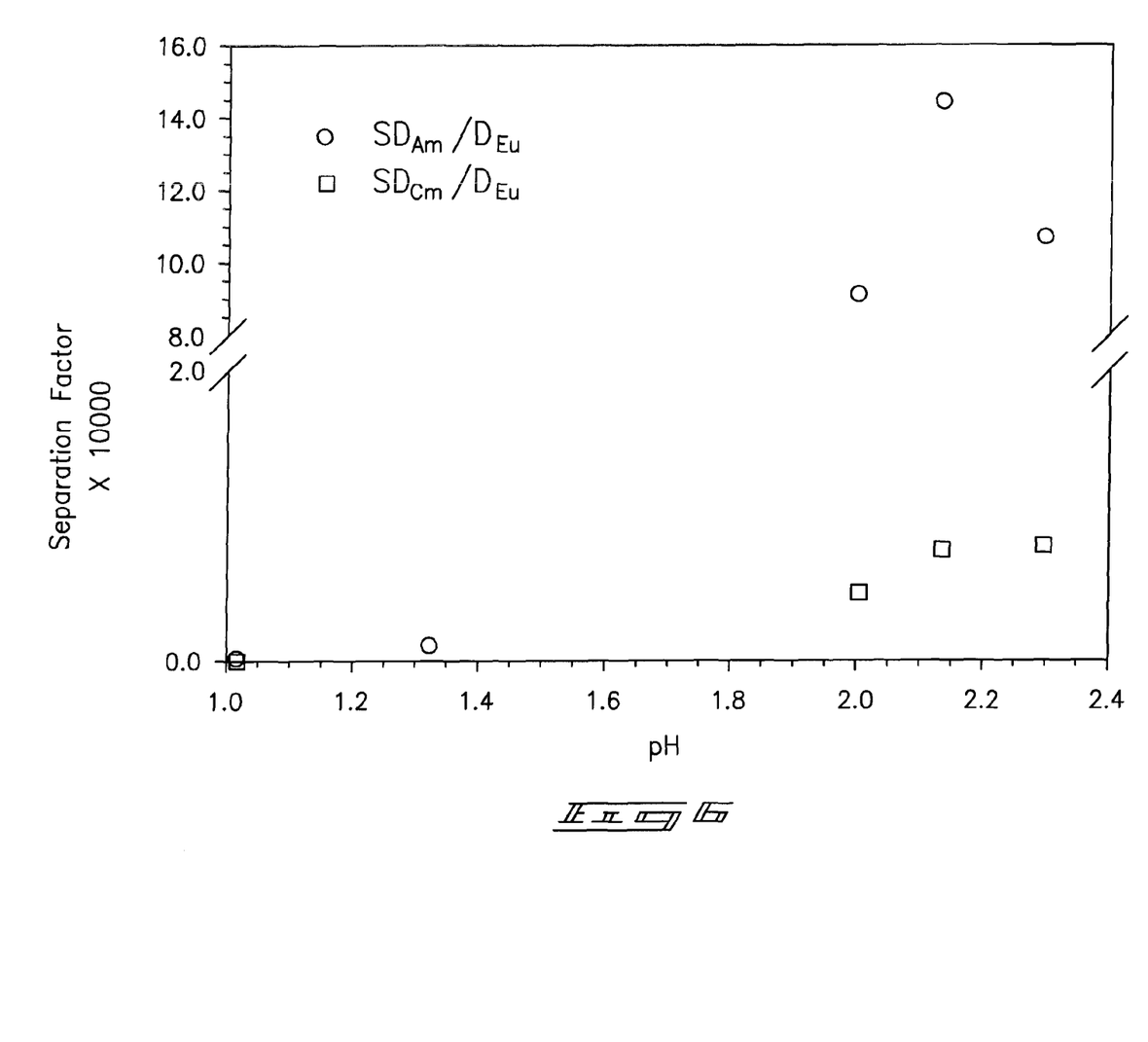
FIG. 6 is a graph showing separation factors ($S=D_{AM}/D_{Eu}$, etc.) as a function of nitric acid concentration.

The separation factors (defined above) for Am(III) from Eu(III), Cm(III) from Eu(III), and Am(III) from Cm(III) determined using radiotracer techniques are presented in Table 6 and FIG. 6. The separation factors for Am relative to Clare not included in FIG. 6 for clarity purposes. The separation factors are calculated using data presented in Tables 1 and 2.

TABLE 6

Separation Factors

| pH | [HNO$_3$], M | S D$_{Am}$/D$_{Eu}$ | S D$_{Cm}$/D$_{Eu}$ | S D$_{Am}$/D$_{Cm}$ |
|---|---|---|---|---|
| 2.30 | 5.0 × 10$^{-3}$ | 1.07E+05 | 7.89E+03 | 1.35E+01 |
| 2.14 | 7.2 × 10$^{-3}$ | 1.44E+05 | 7.56E+03 | 1.90E+01 |
| 1.32 | 4.8 × 10$^{-2}$ | 1.05E+03 | n.d. | n.d. |
| 1.02 | 9.5 × 10$^{-2}$ | 1.21E+02 | 6.20E+01 | 1.95E+00 |

A separation factor significantly greater than 1 is indicative of efficient separation. It should be noted that in the case of both distribution ratios being greater than 1 it is possible to have a separation factor greater than 1 and still not have particularly efficient separation. However, this is not the case for this solvent extraction system (where D$_{Am}$>1 and D$_{Eu}$<1). The data reveals that at a pH greater than 2.0 it is possible to achieve separation factors of greater than S=100,000.

Figure 7:
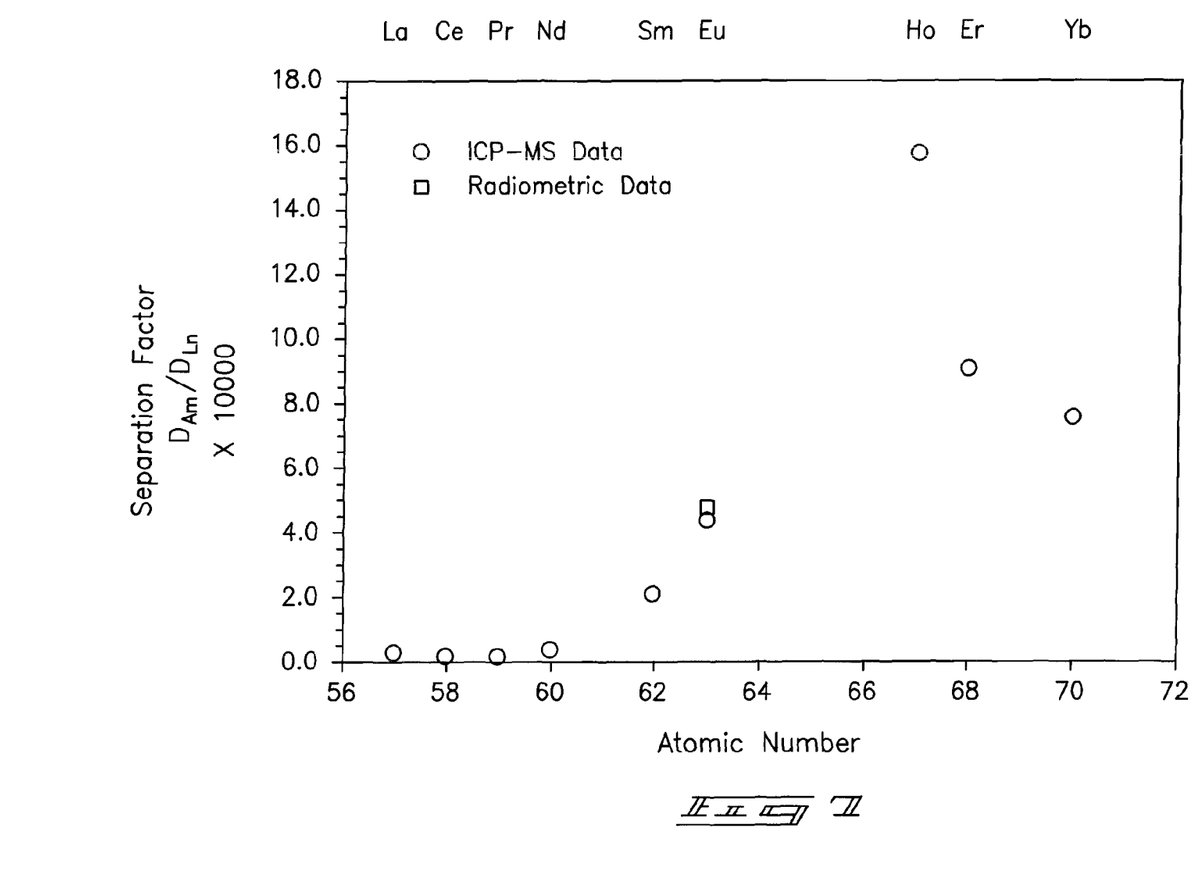
FIG. 7 is a graph showing separation factors for various lanthanide ions in aqueous solution.

Separation factors for Am from the lanthanide ions are presented in Table 7 and are plotted in FIG. 7. These separation factors are calculated utilizing data presented in Tables 1 and 3. In each case the calculated separation factor demonstrates efficient separation of Am(III) from all of the lanthanides in aqueous solution.

TABLE 7

Am Separation Factors

| Ln(III) | S = (D$_{Am}$/D$_{Ln}$) |
|---|---|
| La | 2.84E+03 |
| Ce | 1.08E+03 |
| Pr | 1.29E+03 |
| Nd | 3.34E+03 |
| Pm | n.d. |
| Sm | 2.04E+04 |
| Eu | 4.35E+04 |
| Gd | n.d. |
| Tb | n.d. |
| Dy | n.d. |
| Ho | 1.57E+05 |
| Er | 9.01E+04 |
| Tm | n.d. |
| Yb | 7.51E+04 |
| Lu | n.d. |

Stability studies were performed to determine the stability of dithiophosphinic acids in two-phase separation compositions utilized in accordance with the invention. NMR studies were compared for o-CF$_3$ solutions in contact with acidic solutions and were compared to NMR studies of o-CF$_3$ neat solution phase samples. The results of such stability studies were benchmarked against conventional commercially available CYANEX®-301. Five composition samples were prepared each with 0.1 M o-CF$_3$ in FS-13. These were placed individually in sealed sample tubes with an aqueous phase containing 1.0 M NO$_3$$^-$ (as the sodium salt) and A: 0.100 M H$^+$, B: 0.010 M H$^+$, C, 0.005 M H$^+$, or D: without added acid. A fifth sample, E was a blank sample and was prepared utilizing an organic phase only (no aqueous phase). The samples were placed on a continuous rotation wheel and the phases kept in constant intimate contact.

Figure 8:
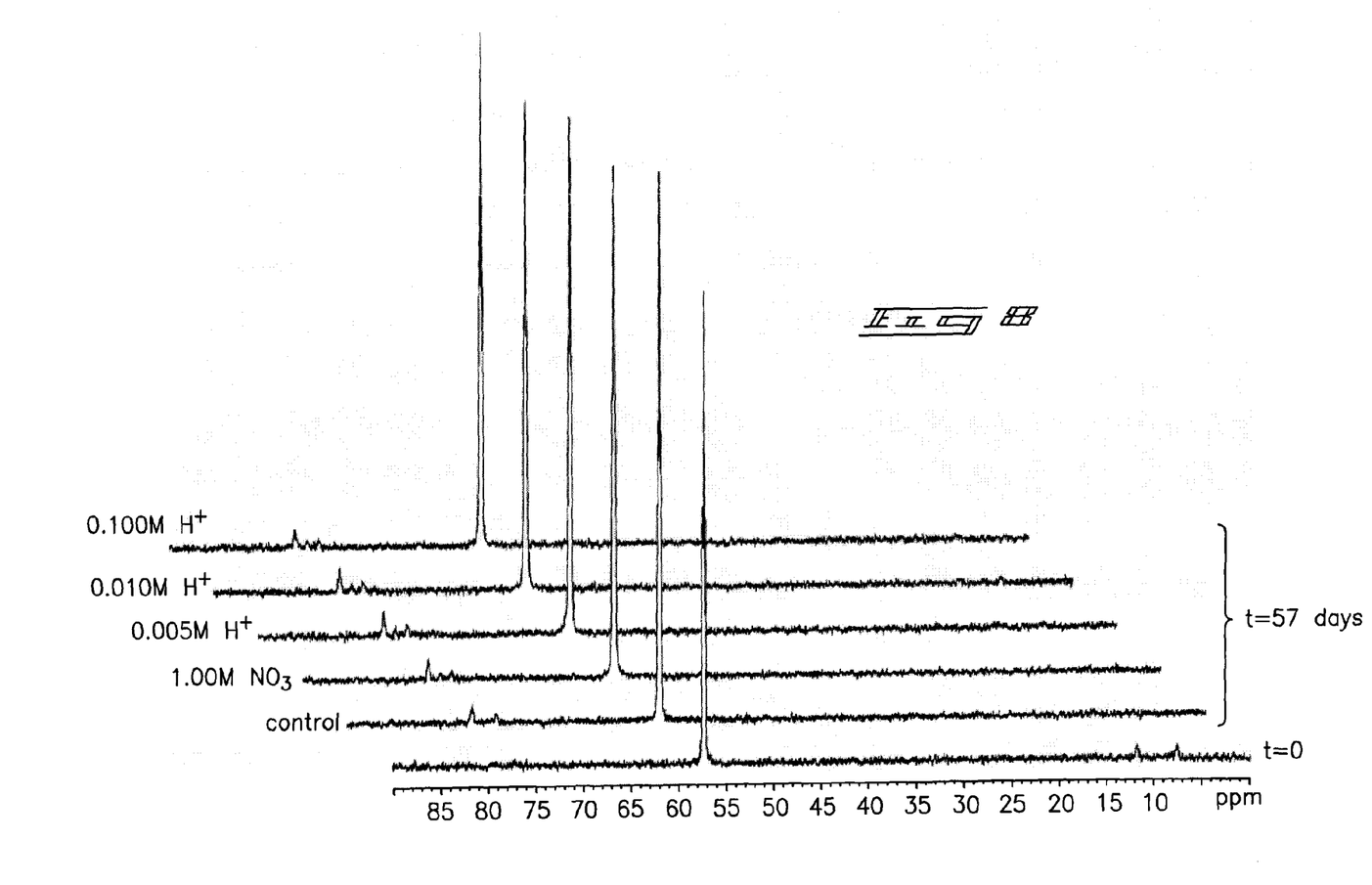
FIG. 8 depicts $^{31}P$ nuclear magnetic resonance (NMR) spectra of bis-(ortho-trifluoromethylphenyl) dithiophosphinic acid in a trifluoromethylphenyl sulfone organic solvent, as initially prepared, or after 57 days of incubation in a two-phase sample system containing an acidic aqueous phase (various [H$^+$]) and a trifluoromethylphenyl sulfone organic solvent phase.
Figure 9:
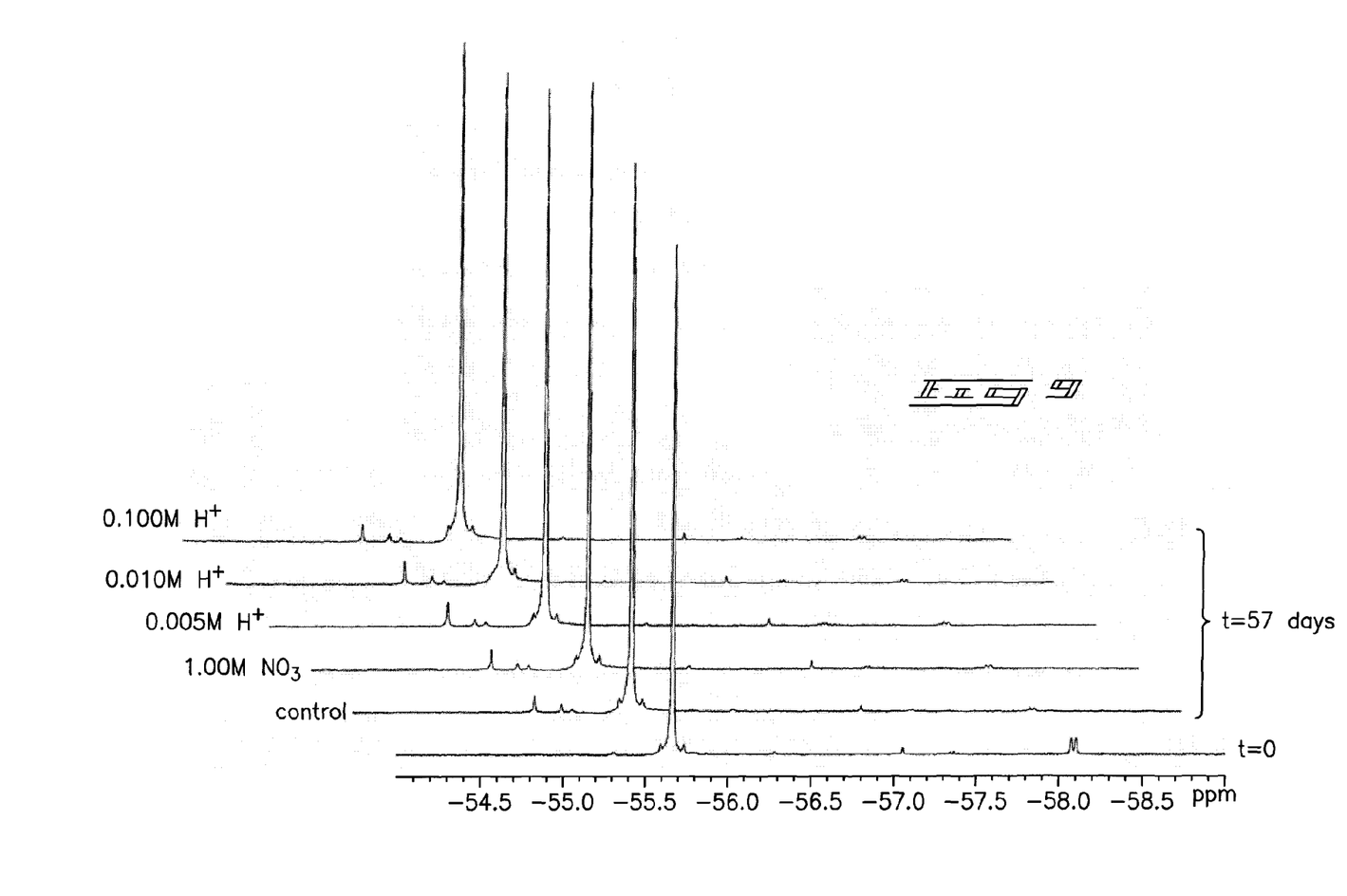
FIG. 9 depicts $^{19}F$ nuclear magnetic resonance (NMR) spectra of bis-(ortho-trifluoromethylphenyl) dithiophosphinic acid in a trifluoromethylphenyl sulfone organic solvent, as initially prepared, or after 57 days of incubation in a two-phase sample system containing an acidic aqueous phase (various [H$^+$]) and a trifluoromethylphenyl sulfone organic solvent phase.

Samples were periodically withdrawn and examined by multinuclear NMR techniques ($^{19}$F and $^{31}$P). The obtained $^{19}$F NMR studies are presented in FIG. 8. The results of the $^{31}$P NMR studies are presented in FIG. 9. The results of these studies were very positive, in that the compound proved to be stable in strong acidic environments for prolonged periods of time. The o-CF$_3$ appears to be stable for weeks at 0.01 M HNO$_3$ and shows little degradation at 0.1 M HNO$_3$, even after months. Additionally, the equilibrium between the organic phase (trifluoromethylphenyl sulfone, CF$_3$, SO$_2$, Ph) and aqueous phase shows that virtually none of the o-CF$_3$ partitions over into the aqueous phase. The new o-CF$_3$ was found to be more stable, not only in contact with molar acid concentrations, but also in solid-phase atmospheric exposure tests in which CYANEX®-301 decomposes noticeably over the given time frame (approximately seven months) where o-CF$_3$ exhibited no detectable decomposition. In general, this stability represents a significant improvement in the state of the art relative to conventional extractants.

The totality of the results indicates that a region-specific/stereo-specific dithiophosphinic acid, such as o-CF$_3$ can effectively separate actinides from lanthanides and can additionally be utilized to separate various actinides from one another. For actinide-actinide separation, an acidic medium can be provided which contains a first actinide and a second actinide. An organic solution containing at least one bisphenyl or alkyl-phenyl dithiophosphinic acid can be added to the acidic medium and the first actinide can be extracted into the organic solution. In particular embodiments, both the first actinide and the second actinide will be extracted into the organic phase. Separation of the organic and the aqueous phases can be utilized to recover the first and second actinides in the organic solution. An additional aqueous phase can then be added to the organic solution where the second aqueous solution has a pH which differs from the original aqueous solution from which the first and second actinide were extracted. Such change in aqueous phase pH can be utilized to effectively re-extract the second actinide into the aqueous phase thereby separating first and second actinides upon removal of the organic phase from the aqueous phase.

For example, an acidic aqueous solution can be provided containing a first actinide (e.g., americium) and a second actinide (e.g., curium). Such solution can optionally contain one or more lanthanides, including but not limited to europium. The pH of the acidic solution can be about 2.3 to 2.5. An organic solution containing o-CF$_3$ can be added to the aqueous solution to form a two-phase separation composition. The o-CF$_3$ can form a complex with Cm(III) and can form a complex with Am(III), and such complexes can be collected by removing the organic phase from the separation composition. A second aqueous phase having a pH of about 2 can be added to the collected organic phase. The Cm(III) can be selectively dissociated from the o-CF$_3$ at this lower pH relative to the Am(III), and can be recovered in the second aqueous phase.

Alternatively, where first and second actinides are present in an aqueous solution, the pH of such an aqueous phase can be such that upon addition of an organic phase containing the bis-phenyl or phenyl-alkyl dithiophosphinic acid, only one of the first and second actinides is extracted into the organic phase. The organic phase can then be removed to isolate the first actinide while the second actinide is retained in the aqueous phase. The pH of the aqueous phase can then be adjusted, followed by addition of a second organic phase containing the same or a differing bis-phenyl or phenyl-alkyl dithiophosphinic acid. The second actinide is then extracted from the aqueous phase under the adjusted pH conditions to isolate the second actinide.

For example, an acidic aqueous solution can be provided containing a first actinide (e.g., americium) and a second actinide (e.g., curium). Such a solution can optionally contain one or more lanthanides including, but not limited to, europium. The acid solution can preferably be provided to have a pH of about 2.0. An organic solution containing o-$CF_3$ can be added to the aqueous solution to form a two-phase separation composition. The o-$CF_3$ can selectively form a complex with Am(III) relative to Cm(III) and lanthanides. Such a complex can then be collected by removing the organic phase from the separation composition. The pH of the aqueous phase can then be adjusted to greater than 2, preferably greater than about 2.14. A second organic solution containing o-$CF_3$ can then be added to the aqueous solution to form a second two-phase separation composition. The Cm(III) can be selectively complexed with o-$CF_3$ relative to the lanthanides, and can be recovered in the second organic phase.

Either of these alternative actinide-actinide separation techniques can be utilized in the presence of one or more lanthanides and can successfully separate actinides from the lanthanides and actinides from each other.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of separating at least one actinide from at least one lanthanide, the method consisting of:
    contacting an acidic medium comprising at least one actinide and at least one lanthanide with an organic solution comprising an organic solvent and bis-(ortho-tri-fluoromethylphenyl)dithiophosphinic acid;
    forming a complex of the bis-(ortho-trifluoromethylphenyl)dithiophosphinic acid and the at least one actinide; and
    extracting the complex of the bis-(ortho-trifluoromethylphenyl)dithiophosphinic acid and the at least one actinide into the organic solution.

2. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium comprising nitric acid, the at least one actinide, and the at least one lanthanide with the organic solution.

3. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium comprising trivalent americium with the organic solution.

4. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium comprising trivalent europium with the organic solution.

5. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium comprising trivalent curium with the organic solution.

6. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium having a pH of greater than or equal to 2 with the organic solution.

7. The method of claim 1, wherein contacting an acidic medium comprising at least one actinide and at least one lanthanide with an organic solution comprising an organic solvent and bis-(ortho-trifluoromethylphenyl)dithiophosphinic acid comprises contacting the acidic medium comprising the at least one actinide and the at least one lanthanide with the organic solution comprising trifluoromethylphenyl sulfone and bis-(ortho-trifluoromethylphenyl)dithio-phosphinic acid.

8. A separation method comprising:
    contacting an acidic medium comprising americium and europium with bis-(ortho-trifluoromethylphenyl)dithiophosphinic acid and trifluoromethylphenyl sulfone;
    forming a complex of the bis-(ortho-trifluoromethylphenyl)dithiophosphinic acid and americium; and
    collecting the complex in the trifluoromethylphenyl sulfone.

9. The separation method of claim 8, wherein contacting an acidic medium comprising americium and europium with bis-(ortho-trifluoromethylphenyl)dithiophosphinic acid and trifluoromethylphenyl sulfone comprises contacting the acidic medium having a pH of from about 2 to about 2.5 with the bis-(ortho-trifluoromethylphenyl)dithiophosphinic acid and trifluoromethylphenyl sulfone.

10. The separation method of claim 8, wherein contacting an acidic medium comprising americium and europium with bis-(ortho-trifluoromethylphenyl)dithiophosphinic acid and trifluoromethylphenyl sulfone comprises contacting the acidic medium comprising at least one additional lanthanide with the bis-(ortho-trifluoromethylphenyl)-dithiophosphinic acid and trifluoromethylphenyl sulfone.

11. The separation method of claim 8, wherein contacting an acidic medium comprising americium and europium with bis-(ortho-trifluoromethylphenyl)dithiophosphinic acid and trifluoromethylphenyl sulfone comprises contacting the acidic medium comprising at least one additional actinide with the bis-(ortho-trifluoromethylphenyl)dithiophosphinic acid and trifluoromethylphenyl sulfone.

12. A method of separating at least one actinide from at least one lanthanide, the method comprising:
    contacting an acidic medium comprising at least one actinide and at least one lanthanide with an organic solvent and bis-(ortho-trifluoromethylphenyl)dithiophosphinic acid;

forming a complex of the bis-(ortho-trifluoromethylphenyl)dithiophosphinic acid and the at least one actinide; and extracting the complex of the bis-(ortho-trifluoromethylphenyl)dithiophosphinic acid and the at least one actinide into the organic solvent.

13. A method of separating at least one actinide from at least one lanthanide, the method comprising:

contacting an acidic medium comprising at least one actinide and at least one lanthanide with an organic solvent, bis-(ortho-trifluoromethylphenyl)dithiophosphinic acid, and at least one other dithiophosphinic acid compound;

forming a complex of the at least one actinide and the bis-(ortho-trifluoromethylphenyl)dithiophosphinic acid or the at least one other dithiophosphinic acid compound; and extracting the complex of the at least one actinide and the bis-(ortho-trifluoromethylphenyl)dithiophosphinic acid or the at least one other dithiophosphinic acid compound into the organic solvent.

* * * * *

UNITED STATES PATENT AND TRADEMARK OFFICE
CERTIFICATE OF CORRECTION

PATENT NO. : 7,799,293 B2  Page 1 of 1
APPLICATION NO. : 11/530508
DATED : September 21, 2010
INVENTOR(S) : Dean R. Peterman et al.

It is certified that error appears in the above-identified patent and that said Letters Patent is hereby corrected as shown below:

In the specification:
COLUMN 3, LINE 46, change "(o-CF$_3$" to --(o-CF$_3$)--

Signed and Sealed this
Twenty-third Day of July, 2013

Teresa Stanek Rea
*Acting Director of the United States Patent and Trademark Office*